United States Patent
Schmidt et al.

(10) Patent No.: US 7,652,181 B1
(45) Date of Patent: Jan. 26, 2010

(54) ALKYLATION REACTOR DESIGN WITH EFFLUENT RECYCLE AND IMPURE BENZENE REGENERATION

(75) Inventors: Robert J. Schmidt, Barrington, IL (US); Michael R. Smith, Rolling Meadows, IL (US); Elena Z. Maurukas, Lemont, IL (US); James A. Johnson, Clarendon Hills, IL (US); Laurence O. Stine, Western Springs, IL (US)

(73) Assignee: UOP LLC, Des Plaines, IL (US)

( * ) Notice: Subject to any disclaimer, the term of this patent is extended or adjusted under 35 U.S.C. 154(b) by 134 days.

(21) Appl. No.: 11/415,700

(22) Filed: May 2, 2006

(51) Int. Cl.
*C07C 2/58* (2006.01)
*C07C 6/12* (2006.01)

(52) U.S. Cl. ............... 585/323; 585/447; 585/450; 585/470; 585/901

(58) Field of Classification Search .......... 585/901, 585/447, 450, 323, 470
See application file for complete search history.

(56) References Cited

U.S. PATENT DOCUMENTS

| | | | |
|---|---|---|---|
| 4,169,111 A * | 9/1979 | Wight | 585/323 |
| 4,870,222 A * | 9/1989 | Bakas et al. | 585/323 |
| 5,196,574 A | 3/1993 | Kocal | 562/94 |
| 5,302,732 A | 4/1994 | Steigleder et al. | 554/98 |
| 5,344,997 A | 9/1994 | Kocal | 568/628 |
| 5,675,048 A * | 10/1997 | Zhang et al. | 585/467 |
| 5,877,370 A | 3/1999 | Gajda | 585/467 |
| 6,069,285 A * | 5/2000 | Fritsch et al. | 585/449 |
| 6,111,158 A | 8/2000 | Marinangeli et al. | 585/467 |
| 6,187,981 B1 | 2/2001 | Marinangeli et al. | 585/323 |
| 6,740,789 B1 | 5/2004 | Bozzano et al. | 585/323 |
| 6,872,864 B2 | 3/2005 | Gajda et al. | 585/467 |

* cited by examiner

*Primary Examiner*—Thuan Dinh Dang
(74) *Attorney, Agent, or Firm*—Arthur E. Gooding (57) ABSTRACT

An improved alkylation reactor design is disclosed. The design uses reactor effluent recycle to reduce the difference in temperature across the reaction zone improving selectivity and insuring the maintenance of a liquid phase in the reactor.

19 Claims, 8 Drawing Sheets

ALKYLATION REACTOR DESIGN WITH EFFLUENT RECYCLE AND IMPURE BENZENE REGENERATION

FIELD OF THE INVENTION

This invention relates to a process and reactor design for producing monoalkyl aromatic compounds by alkylation. Specifically, this invention relates to highly-selective alkylation and transalkylation to produce cumene and ethylbenzene.

BACKGROUND OF THE INVENTION

Monoalkylated aromatic compounds are important for a variety of uses, especially as intermediate compounds in the manufacture of detergents. Two common reactions for producing monoalkylated aromatic compounds are alkylation of aromatic compounds, and transalkylation of polyalkylated aromatic compounds. Monoalkylated aromatic compounds include linear alkylbenzenes (LAB), which are used to form linear alkylbenzene sulfonates (LABS), a common compound used in detergents. Monoalkylated aromatic compounds also include such compounds as ethylbenzene and cumene which are important precursors for the production of styrene and phenols.

Monoalkylated benzenes are formed by reacting benzene with an olefin compound over a catalyst. One such catalyst is beta type zeolites and has been used for benzene alkylation commercially since 1996. Since then new catalysts have been developed and along with a better understanding, new processes. One aspect of benzene alkylation has been the use of high benzene to olefin ratios for the production of alkylbenzene production.

Currently, monoalkylated benzenes are desired, and polyalkylated benzenes are by-products that need to be removed or need to be recycled to try and produce more monoalkylated benzenes. The method of reducing the amount of polyalkylated benzenes is to increase the benzene to olefin ratio. However, the industry is striving to reduce the benzene to olefin ratio in order to save recycle fractionation and energy cost, and the usual method is to use many small beds with decreasing ratios as the benzene and olefins pass through successive beds, yet the lowest ratios tend to be about 5 at the final beds in the process.

Improvements in the process can save raw materials, energy, and reduce costs.

SUMMARY OF THE INVENTION

The invention provides a process for producing monoalkylated aromatic compounds while using a low benzene to olefin ratio in the process. The process comprises passing an aromatic compound to an alkylation reactor and an olefinic compound is passed to the alkylation reactor thereby generating an effluent stream comprising a monoalkylated aromatic compound. A first portion of the effluent stream is passed to a separation zone, thereby generating a product monoalkylated stream, an aromatic stream, and a non-product alkylated aromatic stream. A second portion of the effluent stream from the alkylation reactor is recycled to the inlet of the alkylation reactor.

In one embodiment, the process comprises passing the aromatic compound and the olefinic compound to the alkylation reactor at a molar ratio less than 2.5.

In another embodiment, the process comprises passing the second portion of the effluent stream to the alkylation reactor in an amount greater than 50% of the effluent stream.

Other objects, advantages and applications of the present invention will become apparent to those skilled in the art from the following drawings and detailed description.

DETAILED DESCRIPTION OF THE INVENTION

Alkylated aromatic compounds have important commercial utility. The general process for alkylation is known, and takes place in an alkylation reactor. The alkylation reactor comprises a solid alkylation catalyst, and is operated under conditions for the alkylation reaction to take place. Two examples of important alkylated aromatics are ethylbenzene, used in the production of styrene, and cumene, used in the production of phenol. Improvements in the production of alkylated aromatics increase selectivity and conversion leading to savings in cost and raw materials.

It has been discovered that efficient use of effluent recycle is a key parameter in maintaining an alkylation reactor under stable conditions, while operating the reactor at a low benzene to olefin ratio. Currently, in order to obtain high olefin conversion, greater than 95%, alkylation units are operated at benzene to olefin ratios from 3 to 10, and typically around 5. Recycling of the effluent stream is shown in U.S. Pat. No. 6,872,864, issued Mar. 29, 2005, and which is incorporated by reference. However, the recycling is to minimize olefin concentrations to the inlet and is a means of achieving better catalyst stability, yet fails to consider the use of recycle at high rates and very high catalyst space velocities. In addition, the recycling of the product stream is recommended to be limited in the prior art, and does not indicate any benefit from higher recycle rates. Using high recycle rates and high catalyst space velocities allows for olefin breakthrough, which the prior art seeks to prevent, and achieves high selectivity. When olefin breakthrough is allowed, the alkylation selectivity of the monoalkylate product approaches equilibrium at low benzene to olefin ratios.

In contrast, the prior art seeks 100% olefin conversion by using high benzene to olefin ratios, and designs the process to have no olefin breakthroughs. The use of effluent recycle maintains the desired high olefin conversion, while reducing the benzene to olefin ratios, and provides for longer catalyst life.

By recycling the effluent stream, the process provides more control over the alkylation reaction. With a high effluent recycle, the ratio of benzene to olefins are kept to a level of less than about 2.5 by molar ratio. Preferably, the process is operated at a benzene to olefin ratio between about 1.3 to about 2.0, with a most preferred operational ratio of about 1.5. This process also allows for high space velocities of the catalyst, and allows for olefin breakthroughs while achieving high alkylation selectivity, and maintaining a liquid phase in the reactor.

The process of the present invention for benzene alkylation reactors is operated at a temperature from about 120° C. to about 250° C., and preferably from about 150° C. to about 230° C. The reaction is exothermic, and the temperature in the reactor rises with residence time. By increasing the recycle rate, the temperature rise in the reactor is reduced, and the recycle rate should be sufficient to reduce the change in temperature during the reaction into the range from about 5° C. to about 50° C., with the recycle rate preferably sufficient to reduce the temperature change to less than about 40° C.

The high effluent recycle, in addition to maintaining a low benzene to olefin ratio, contributes to reducing temperature swings, and temperature increases across the reactor during the process. The process also produces a flatter temperature profile along the length of the reactor, resulting in lower outlet temperatures of the effluent from the reactor. The maintenance of a lower temperature profile along the reactor produces a higher yield. In addition, the recycling of effluent can reduce the amount of intercooling needed in a multibed process.

Catalysts for use in this invention are solid acid catalysts that include, but are not limited to, amorphous and crystalline alumino-silicates, clays, ion-exchange resins, mixed oxides, and supported acids, and Friedel-Crafts-type catalysts such as $AlCl_3$. Among these solid acid catalysts, ZSM-5, Y-type zeolites, and more recently MCM-22, beta-zeolite, and UZM-8 have become the new commercial catalysts of choice for aromatic alkylation. Catalysts usable in the present invention include shape selective large pore zeolites with the active sites located predominantly in the pores such as beta zeolites, and moderate sized pore zeolites with active sites external as well as internal to the pores such as MWW zeolites.

The following examples are exemplary, and the aromatic feed is a benzene feed, with an olefinic feed of ethylene, and a product alkylated aromatic compound of ethylbenzene. Non-product alkylated aromatic compounds in the examples include polyethylbenzene, or other polyalkylated aromatic compounds. While the examples use benzene and ethylene, this does not preclude the use of other aromatic compounds, or other olefinic compounds, especially propylene, for use in configurations covered by these embodiments.

Embodiment 1

Figure 1:
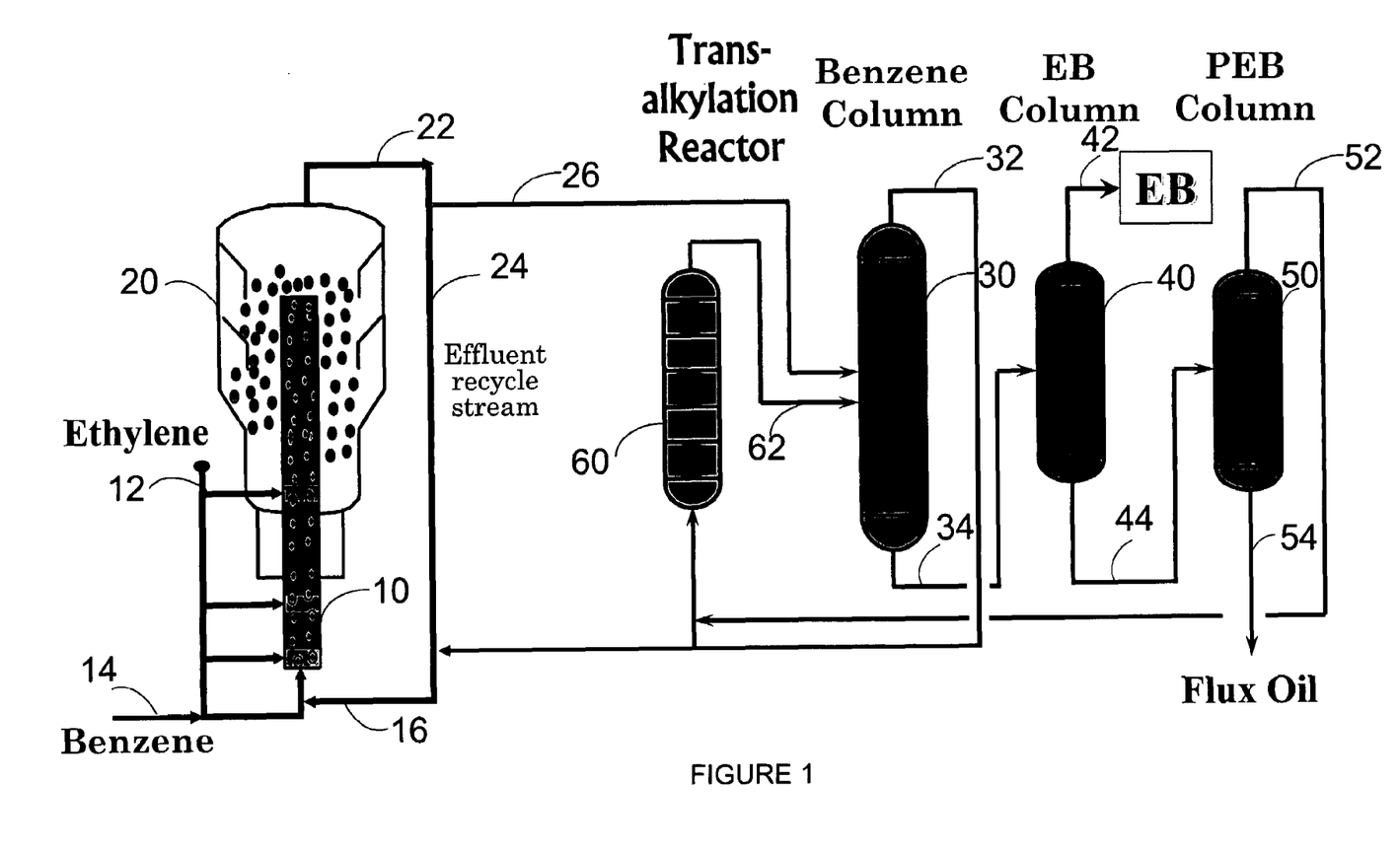
FIG. 1 is a first embodiment of the process.

In one embodiment, as shown in FIG. 1, the aromatic alkylation process uses a liquid riser reactor 10 operating with a high effluent recycle rate to the riser reactor 10. The riser reactor 10 has a feed of ethylene 12, benzene 14 and effluent recycle 16 to the riser reactor 10. The effluent disengages from the catalyst in a separation section 20, and an effluent stream 22 is split into a recycle stream 24 and a separation feedstream 26. The separation zone comprises a first separation, or benzene column 30, a second separation, or monoalkylated benzene column 40, and a third separation, or polyalkylated benzene column 50. The separation feedstream 26 is a portion of the effluent stream 22, and is separated into a product stream 42, comprising an alkylated aromatic compound, an aromatic stream 32, comprising an aromatic compound, and a non-product alkylated aromatic stream 52. In this embodiment, the aromatic stream 32 comprises benzene, the product stream 42 comprises ethylbenzene, and the non-product alkylated aromatic stream 52 comprises polyethylbenzene.

The separation of the product stream 42 from the portion of the effluent stream 22 directed to the separation zone comprises directing the separation feedstream 26 through a benzene column 30, thereby separating the feedstream into a benzene stream 32 and a first bottoms stream 34. A portion of the benzene stream 32 is directed to a transalkylation reactor 60, while the remainder of the benzene stream 32 is recycled to the alkylation reactor 10. The first bottoms stream 34 is directed to the monoalkylated benzene column 40, separating the first bottoms stream 34 into a monoalkylated product stream 42, and a second bottoms stream 44. The second bottoms stream 44 is directed to the polyalkylated benzene column 50, separating the second bottoms stream 44 into a polyalkylated benzene stream 52 and a heavies stream 54. The heavies stream 54 for the ethylbenzene process is known as flux oil. The polyalkylated benzene stream 52 is directed to the transalkylation reactor 60, wherein the benzene and polyalkylated benzene are reacted to produce a transalkylation effluent stream 62 comprising monoalkylated benzene. The transalkylation effluent stream 62 is directed to the benzene column 30 to separate the monoalkylated benzene from the transalkylation effluent.

Figure 2:
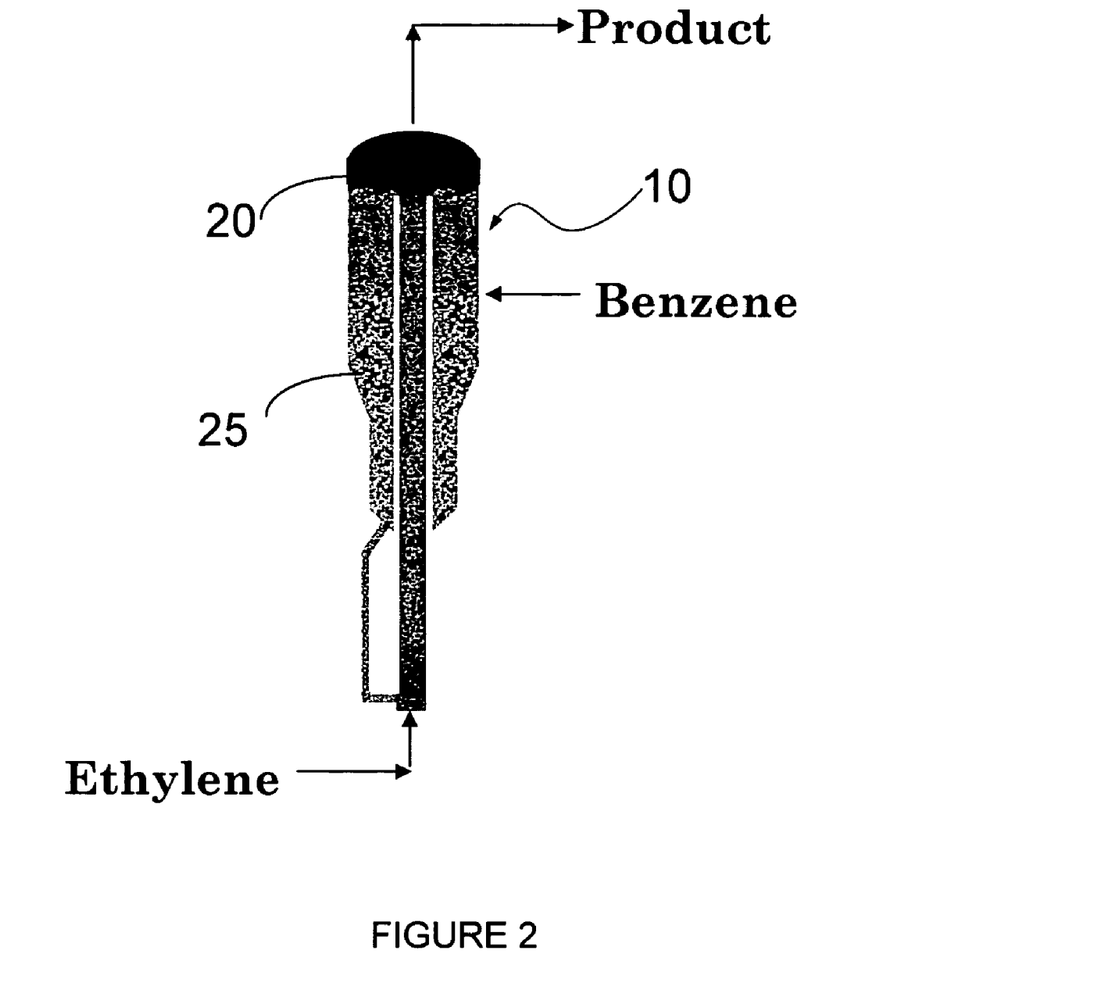
FIG. 2 is an alternate design for the riser reactor of the first embodiment.

The use of a riser reactor for the alkylation reactor 10 provides the opportunity to regenerate the catalyst during the process. As shown in FIG. 2, the alkylation catalyst separates from the product stream in a separation section 20, and the catalyst is collected and regenerated in a regeneration section 25. The addition of benzene to the regeneration section 25 improves the catalyst regeneration. The benzene and catalyst reenter the reactor with ethylene. The riser reactor system for ethylbenzene production reduces operating and capital costs while maintaining high selectivity for olefin conversion.

The riser reactor is operated with catalyst and liquid residence times between about 1 minute and about 10 minutes. It is preferred that the olefin injection is done at a plurality of points along the height of the reactor, with the number of injection points from 2 to 6, with a preferred number of injection points from 4 to 6. The process further includes operation of the reactor at catalyst to olefin ratios from about 0.2 to about 1.0 by weight.

This operation uses a high effluent recycle rate of the effluent recycle stream 24 and improves the monoalkylate selectivity and maintains a lower benzene to olefin ratio over existing fixed bed systems. The high effluent recycle provides additional lift liquid for the catalyst and saves substantial fresh benzene cost.

The process of using a high effluent recycle rate is useful in extending the life of fixed bed catalysts also. This provides for improving existing reactors without replacing the reactors, and thereby improving performance.

Embodiment 2

Figure 3A:
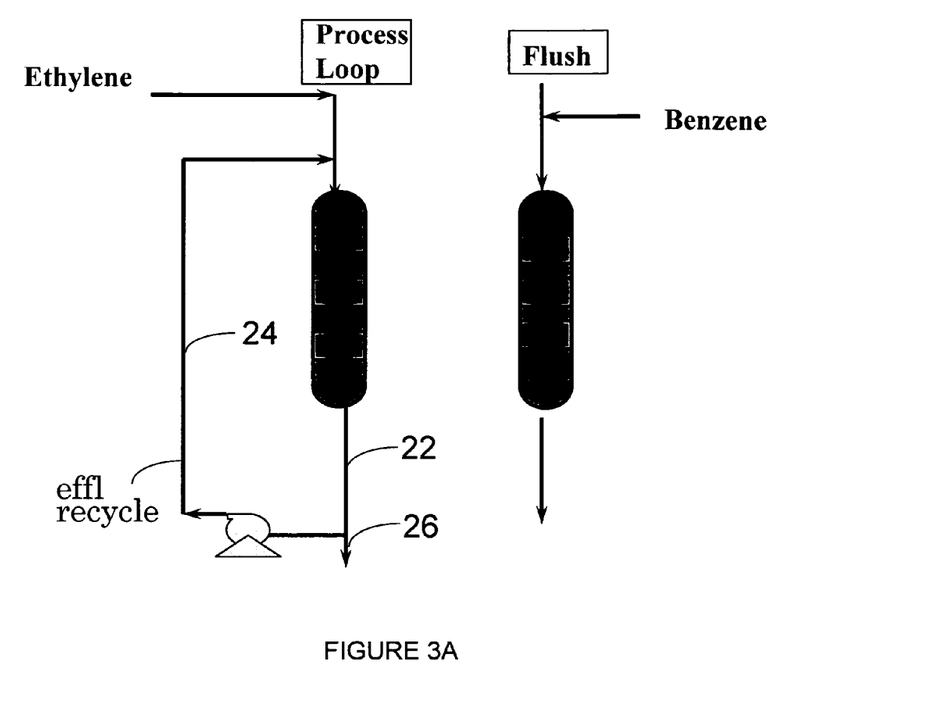
FIG. 3a is an embodiment using a fixed bed design.

The use of a recycle stream works with a fixed bed alkylation reactor as shown in FIG. 3a. The use of a high recycle of the effluent stream from the alkylation reactor maintains a high conversion rate at olefin breakthrough, while allowing the operation with a low benzene to olefin ratio. This is operated at a high space velocity, and can reduce the amount of catalyst, in comparison with a conventional fixed bed, to between ⅓ and ⅕ of the amount of catalyst. In this embodiment, the process comprises a swing bed/cyclic operation. The operation uses a very high effluent recycle rate to maintain the alkylation reaction of the aromatic compound at olefin breakthrough. The process is operated at a very high space velocity and uses between 20% and 35% of the amount of catalyst of a conventional fixed bed alkylation process. One benefit of this embodiment is the operation at a lower inlet temperature, with the alkylation reactor bed operated at a more uniform temperature, and that there is a lower temperature increase across the reactor. This embodiment is coupled with periodic hot benzene washes and can take advantage of using recycled benzene recovered from the benzene column. The benzene wash conditions are at temperatures from about 220° C. to about 260° C., with the temperatures preferably between 225° C. and 250° C., and most preferably about 230° C.

The process comprises recycling a portion 24 of the effluent stream 22 with fresh makeup benzene at a rate from 20 to 50 times the amount of ethylene feed by weight, with a preferred rate of about 35 times. The reaction cycle is followed by a flush cycle comprising benzene. The flush stream can include the effluent stream, and benzene from the benzene column and fresh benzene. The reaction cycle is operated for 5 to 10 minutes, with a flush cycle operated for 1.5 to 5 minutes, with a preferred operation of a reaction cycle of about 7 minutes and a flush cycle of about 3 minutes.

With a fixed bed reactor, the catalyst within the reactor is periodically regenerated. The process with a fixed bed reactor comprises operating the reactor with periodic flushes and benzene washes. A typical operation cycle, as shown in FIG. 3a, can comprise running the reactor with an ethylene injection for about 10 minutes, with an effluent recycle 24 of about 35 times of the product stream draw-off 26. The ethylene injection is stopped, and a benzene flush is performed lasting about 2 to 3 minutes, during a non-regeneration mode. Then the process is repeated.

Figure 3B:
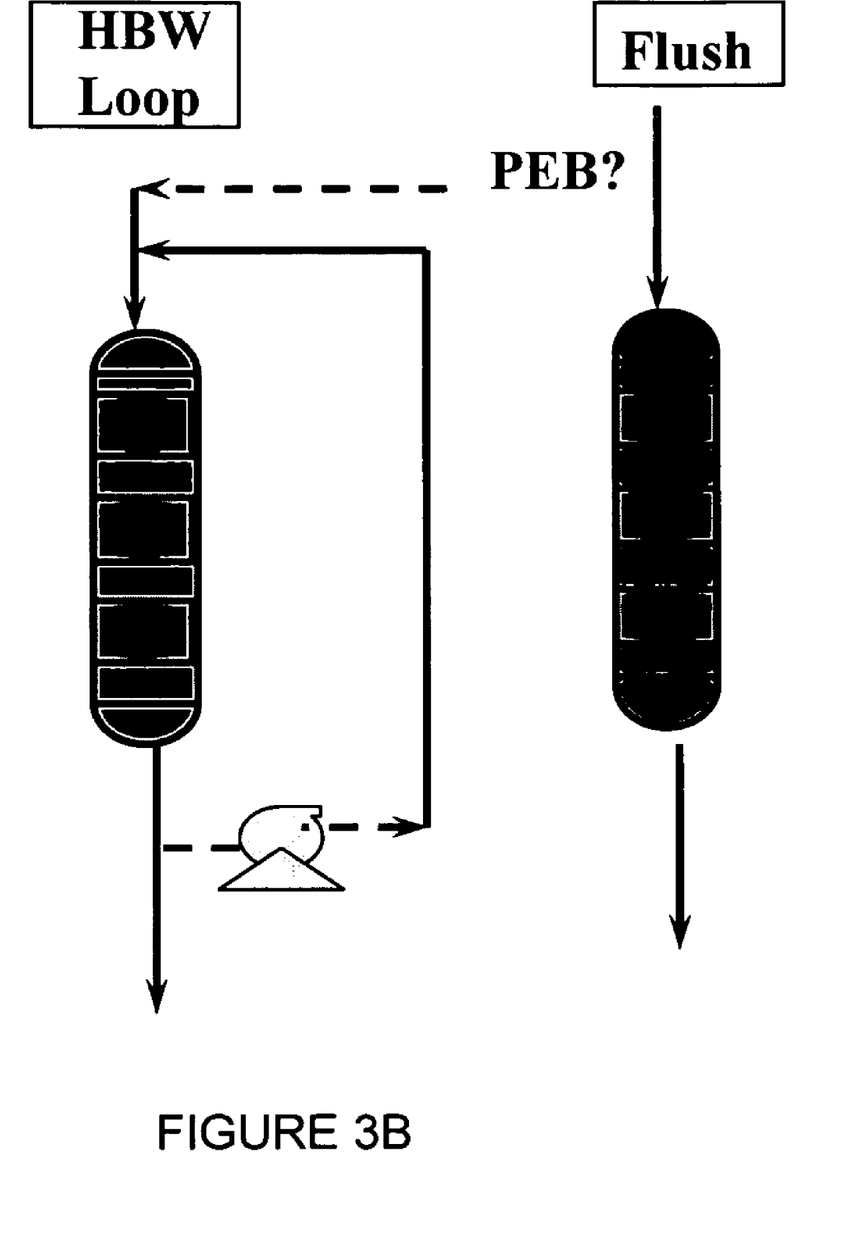
FIG. 3b is an embodiment of the fixed bed design during regeneration.

During a regeneration mode, as shown in FIG. 3b, the ethylene injection is stopped and a regeneration cycle is started. A flush is performed, with continuing recycle, lasting about 12 to 15 minutes. The flush removes the product and unreacted feed out of the reactor before a hot benzene wash. The recycle is followed by a hot benzene wash lasting about 10 to 12 minutes and then a subsequent flush from about 3 to 4 minutes. If the regeneration cycle is repeated, the initial flush on subsequent cycles is increased up to about 1 hour, depending on operation conditions. The high recycle facilitates controlling temperature changes during cycle changes.

For this swing bed-cyclic operation, the effluent recycle is used to limit the conversion to 95-99.5% at low benzene/ethylene ratio. When the conversion reaches the target level, the product is flushed from the catalyst zone, and a hot benzene wash (HBW) step is used to rejuvenate the catalyst. The HBW is repeated to remove any heavier by-products that have accumulated during the process step. This includes the formation of additional ethylbenzene that occurs as a result of the HBW step.

Embodiment 3

Figure 4:
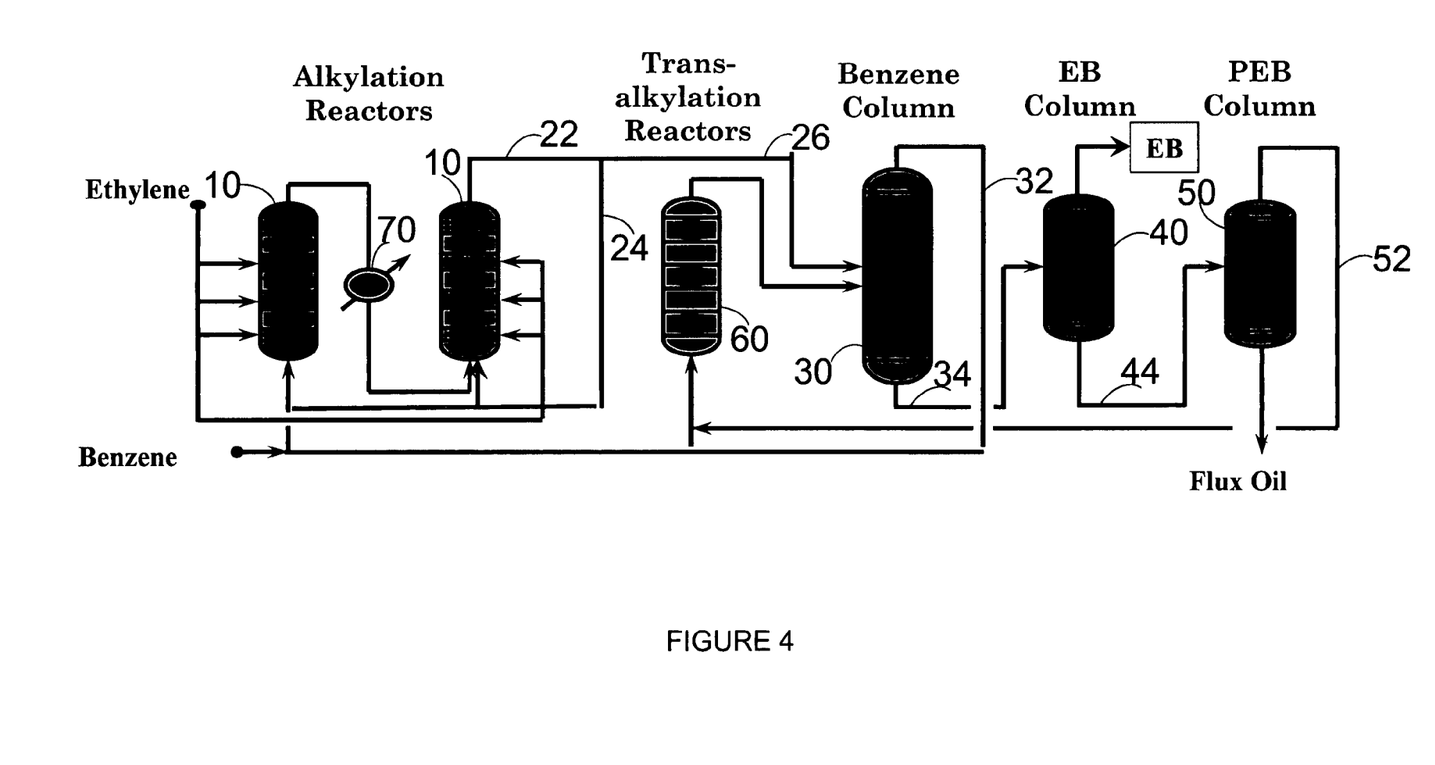
FIG. 4 is an embodiment of a series of fixed bed reactors with recycle to each reactor.

An alternate fixed bed scheme comprises using a plurality of alkylation reactors in series. FIG. 4 shows the configuration with two alkylation reactors 10 in series, with a recycle stream 24 split to send a portion of the recycle stream 24 to each reactor 10. The amount of recycle to each reactor can be varied to optimize control over the temperatures in the reactors. In each reactor 10, there are a plurality of ethylene inputs, injected into distributors before flowing over a catalyst bed. The process includes a heat exchanger 70 for removing some excess heat generated during the reaction, and to control the reactor 10 inlet temperature. In the multiple fixed bed flow scheme, a portion 26 of the effluent stream 22 is directed to a separation unit for recovery of the ethylbenzene product. The separation unit comprises a benzene column 30 for recovering and recycling unreacted benzene. The benzene column 30 produces a benzene stream 32 and a first bottoms stream 34. The unreacted benzene is recycled to the alkylation reactors 10 and a portion is directed to a transalkylation reactor 60. The first bottoms stream 34 is directed to an ethylbenzene column 40 for separation and recovery of the product, ethylbenzene. The ethylbenzene column generates a second bottoms stream 44 which is directed to a polyethylbenzene column 50 for recovery of polyethylbenzene. The polyethylbenzene stream 52 is directed to the transalkylation reactor 60 with the benzene and reacted to generate more ethylbenzene. The multibed scheme allows for a single bed to be taken off-line, and the catalyst regenerated with a benzene flush, or with benzene and recycle stream flush, while the other beds remain on-line.

Embodiment 4

Figure 5:
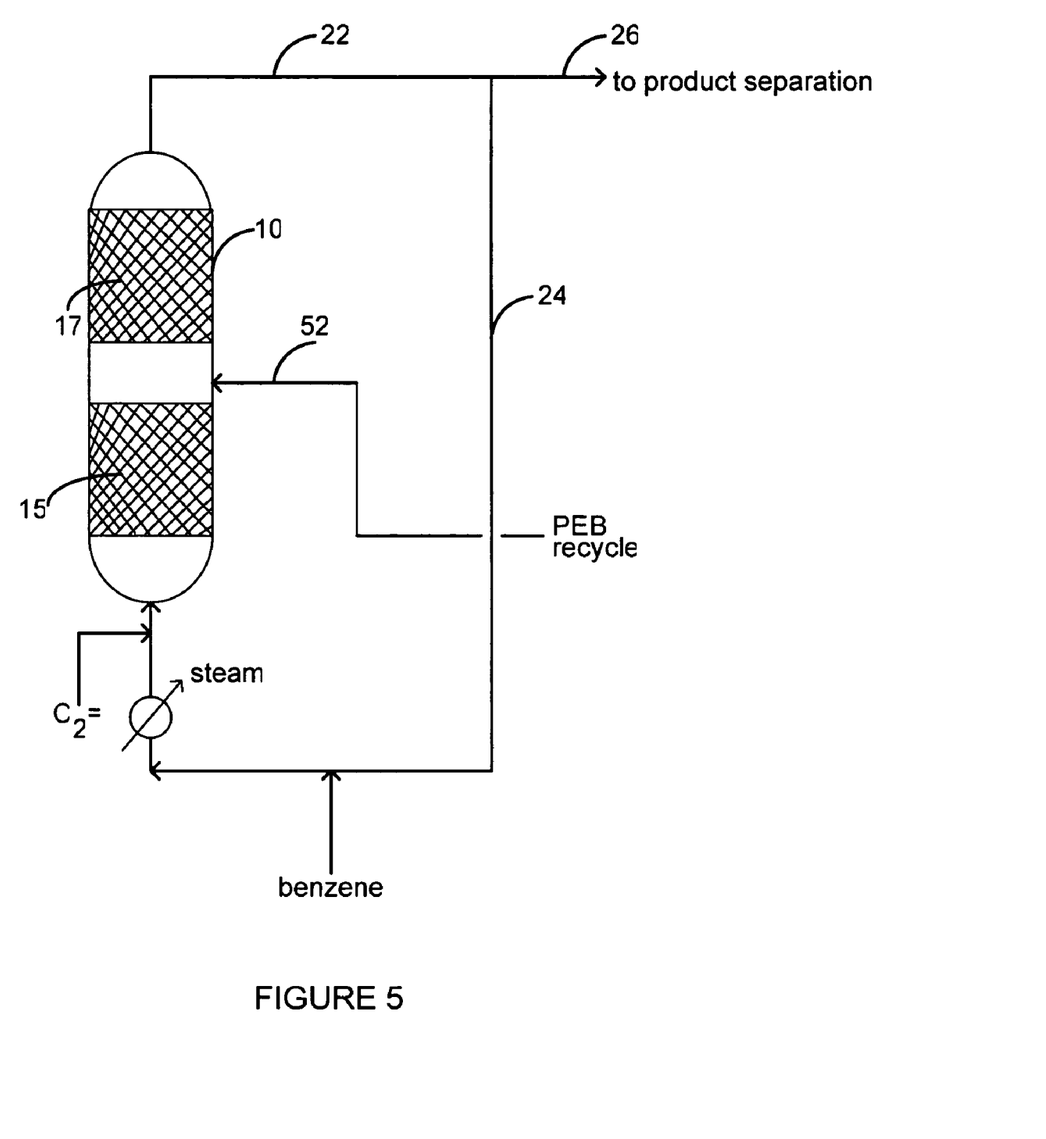
FIG. 5 is an embodiment of an alkylation and transalkylation reactor in series with recycle.

The fixed bed reactor with a high recycle rate of the effluent stream provides the opportunity for operation of the alkylation reactor in series with a transalkylation reactor before sending a portion of the effluent stream to the product separation section. One possible arrangement is shown in FIG. 5. The reactor 10 comprises an alkylation catalyst bed 15 followed by a transalkylation catalyst bed 17. The effluent stream 22 is split into a recycle stream 24 and a stream 26 directed to a product separation unit (not shown). Benzene is added as makeup for the ethylbenzene removed as product from the stream 26 directed to the product separation unit. The recycle stream 24 is fed into the reactor and passed over the alkylation catalyst bed 15 and the transalkylation catalyst bed 17. The recycle stream 24 provides control over the temperature rise in the catalyst beds. An intermediate feed 52 of recovered polyethylbenzene (PEB) can be injected into the reactor before the transalkylation catalyst bed. This recycles the PEB to improve the ethylbenzene yield.

Embodiment 5

The series reactors with recycle can be incorporated into aluminum chloride (AlCl$_3$) alkylation reactors. This combination of an alkylation/transalkylation reactor can be a result of the catalyst and the operating conditions of the reactor. One such catalyst is aluminum chloride in the alkylation unit, the alkylator and transalkylator are combined in a single unit 10. The effluent stream 22 is mixed with benzene and is split to a recycle stream 24 and a stream 26 directed to effluent wash and product separation unit (not shown). The product separation unit provides a polyethylbenzene (PEB) stream 52 which is recycled to the reactor 10. The aluminum chloride reactor unit includes a catalyst separation drum 80 for separating and collecting catalyst to be treated and recycled.

The recycle stream 24 is recycled at a high rate, generally at a rate where the feed to the alkylation reactor is more than 50% recycled effluent, and preferably at a rate where the feed to the alkylation reactor is more than 90% recycled effluent. With all the embodiments, ethylene is mixed with the alkylation reactor feed, and is fed at a rate to give a benzene to ethylene molar ratio of less than 2.5, with a preferable ratio of benzene to ethylene between about 1 and about 2. The high recycle rate not only controls the delta temperature for the reactor, but also compensates for the low selectivity that results from the low benzene/ethylene ratio by limiting conversion to 95 to 99.5%. The high recycle rate also facilitates the solubility of ethylene in the feed hydrocarbon mix at low benzene/ethylene ratio to ensure that all feed and product components remain in the liquid phase during the course of the reaction. In addition, the present invention overcomes the limited partial conversion of heavier di- and tri-alkylated species to the ethylbenzene product, when operating at a low benzene to ethylene ratio. This is in contrast to the current industry which maintains high benzene to ethylene ratios to minimize heavy polyalkylated species formation, and which under prevailing conditions does not completely convert to ethylbenzene.

Figure 6:
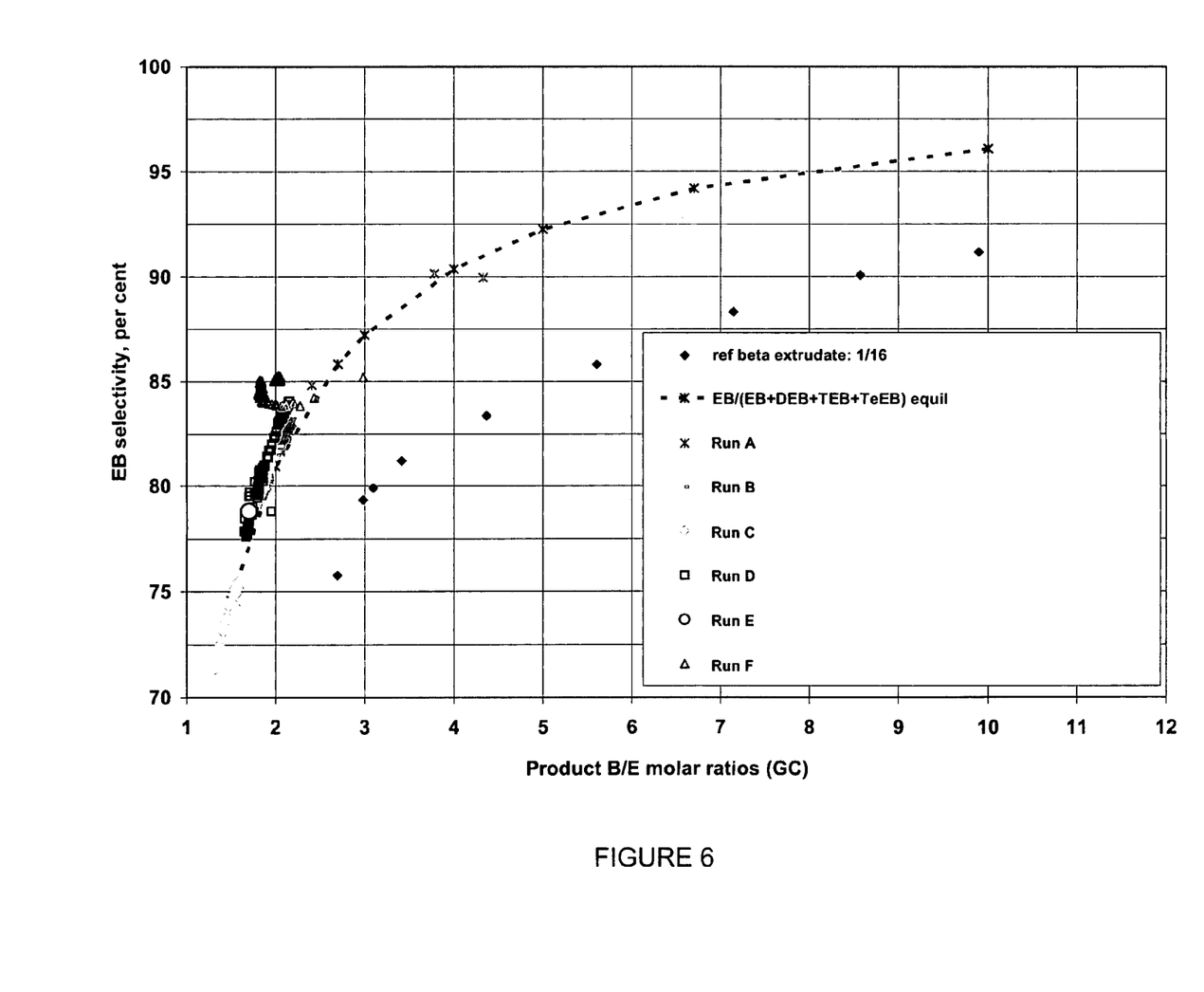
FIG. 6 shows the results for ethylbenzene synthesis with riser reactor.

The results of numerous runs are shown in FIG. 6. A fixed bed reactor using a reference beta zeolite was run. The conditions for the fixed bed had a pressure of 3.9 MPa (550 psig), an ethylene WHSV of 1.98 hr$^{-1}$. The feed B/E molar ratio was 2.7. The reference beta catalyst in the fixed bed must be stopped before ethylene breakthrough and the catalyst regenerated. The product B/E ratio decreased over time and approached the limit of 2.7 which is the feed ratio. The selectivity also dropped off over time. This is a similar response seen in commercial reactors, however the commercial reactors generally have a much higher B/E feed ratio to delay ethylene breakthrough. With riser reactors, using a commercial catalyst, the high recycle to feed ratio improved selectivity as well as produced much lower product B/E ratios, and in some cases exceeded equilibrium.

Figure 7:
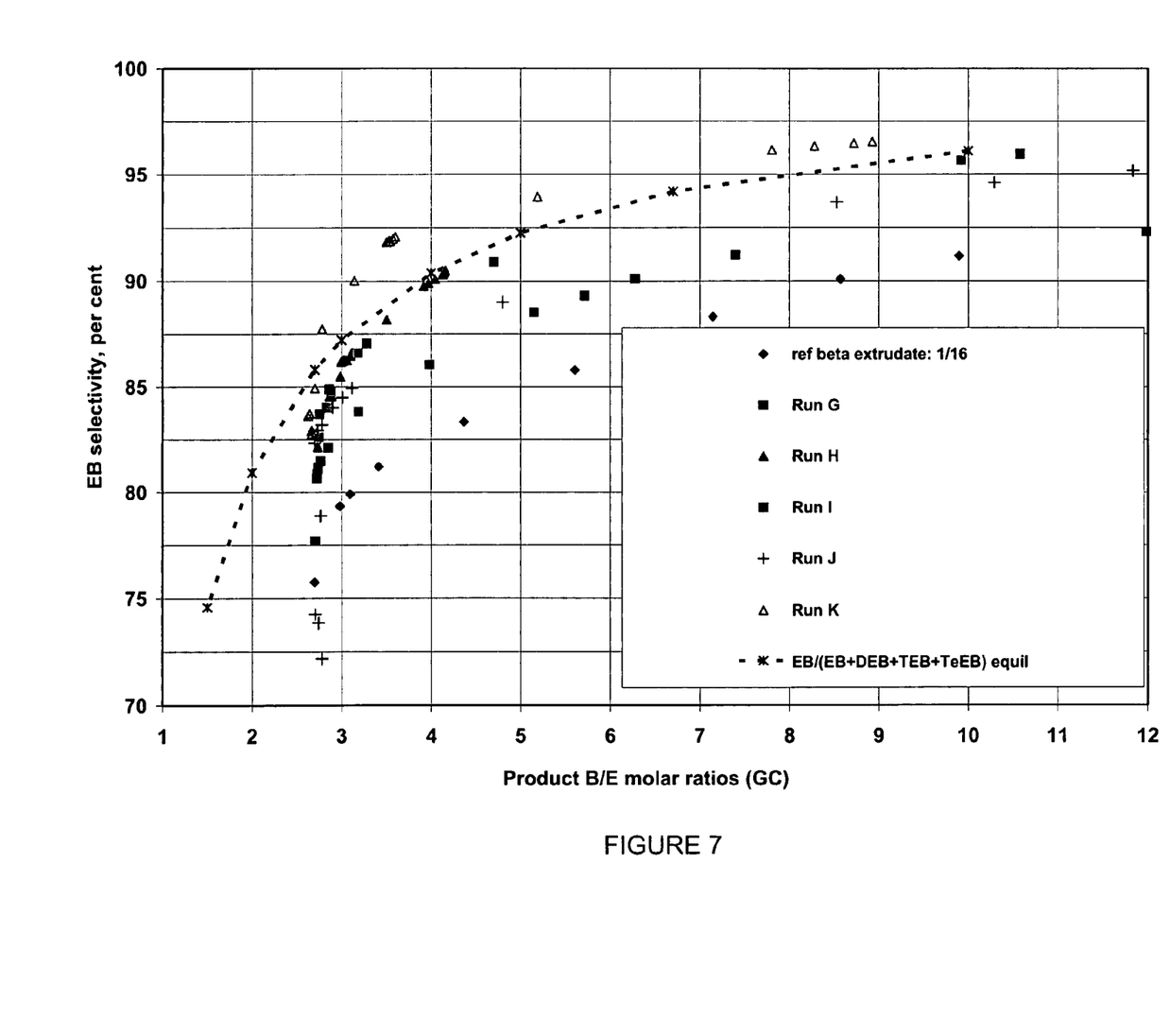
FIG. 7 shows the results for ethylbenzene synthesis with other catalysts in a fixed bed with high recycle.

Even with fixed beds, with the use of commercial catalysts in fixed beds with high recycle, there were significant improvements as shown in FIG. 7. The fixed bed runs also used a feed B/E ratio of 2.7 and was operated at a pressure of 3.9 MPa (550 psig). With high recycle there was an improvement in selectivity. The improvement in selectivity continued through the operation until the runs were terminated as the product B/E ratios approached 2.7.

Operation with high recycle rates can provide substantial economic benefit through improved yields.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for producing a monoalkylated aromatic compound comprising:
   passing an aromatic feedstock comprising an aromatic compound to an alkylation zone of a reactor, and passing an olefinic compound to the alkylation zone, wherein the molar ratio of the aromatic feedstock to the olefinic feedstock is from 1.3 to 2.0, and operated at conditions that allow for olefin breakthrough, thereby generating an alkylation effluent, wherein the olefinic compound is injected in multiple injection ports, and the reactor temperature rise is limited to less than 50° C. through control of an effluent recycle, and wherein the reactor is an alkylation/transalkylation reactor comprising the alkylation zone thereby generating the alkylation effluent and a transalkylation zone, wherein the entire alkylation effluent is passed to the transalkylation zone of the reactor and the effluent stream is from the transalkylation zone of the reactor;
   passing a first aliquot portion of the effluent stream to be separated to a separation zone, thereby generating an aromatic stream, a product monoalkylated aromatic stream, and a non-product alkylated aromatic stream; and
   recycling a second aliquot portion of the effluent stream comprising an alkylated aromatic compound to the alkylation zone.

2. The process of claim 1 further comprising passing a portion of the non-product alkylated aromatic stream to the alkylation reactor.

3. The process of claim 1 further comprising passing a portion of the aromatic stream to the alkylation reactor.

4. The process of claim 1 wherein the alkylation reactor comprises a riser reactor having a catalyst separation section and a catalyst regeneration section.

5. The process of claim 4 further comprising benzene addition to the catalyst regeneration section.

6. The process of claim 1 wherein the molar ratio of aromatic feedstock to olefinic feedstock is about 1.5.

7. The process of claim 1 wherein the second portion of the effluent stream recycled to the alkylation reactor is greater than 50% of the effluent stream.

8. The process of claim 1 wherein the second portion of the effluent stream recycled to the alkylation reactor is greater than 90% of the effluent stream.

9. The process of claim 1 wherein the effluent stream is separated by:
   passing the effluent stream to an aromatic fractionation column, thereby generating an aromatic stream and a first bottoms stream;
   passing the first bottoms stream to a product fractionation column, thereby generating a monoalkylated product stream, and a second bottoms stream;
   passing the second bottoms stream to a polyalkylated aromatic fractionation column, thereby generating a polyalkylated aromatic stream, and a third bottoms stream;
   passing the polyalkylated aromatic stream and a portion of the aromatic stream to a transalkylation reactor, thereby generating a transalkylation product stream comprising monoalkylated aromatic compounds; and
   passing the transalkylation product stream to the aromatic fractionation column.

10. The process of claim 1 where the aromatic compound is benzene.

11. The process of claim 1 where the olefinic compound is ethylene or propylene.

12. The process of claim 1 wherein the product alkylated aromatic compound is ethylbenzene or iso-propylbenzene.

13. The process of claim 1 wherein the alkylation reactor comprises a fixed bed reactor comprising at least one catalyst bed.

14. The process of claim 13 further comprising an intermittent hot benzene wash of the catalyst bed at a temperature greater than 220° C.

15. The process of claim 1 wherein the number of olefinic injection ports is between 2 and 6.

16. A process for producing a monoalkylated aromatic compound comprising:
   passing an aromatic feedstream comprising an aromatic compound to an alkylation zone of a reactor, and passing an olefinic feedstream comprising a monoolefin compound to the alkylation zone, wherein the molar ratio of the aromatic feedstock to the olefinic feedstock is from 1.3 to 2.0, and operated at conditions that allow for olefin breakthrough, wherein the alkylation reactor comprises a solid catalyst and the aromatic compound and monoolefin are reacted in the presence of the catalyst at reaction conditions, thereby generating an alkylation effluent, and wherein the olefinic feedstream is injected in multiple injection ports, and the reactor temperature rise is limited to less than 50° C. through control of an effluent recycle, and wherein the reactor is an alkylation/transalkylation reactor comprising an alkylation zone thereby generating the alkylation effluent and a transalkylation zone where the entire alkylation effluent is passed to the transalkylation zone of the reactor and the effluent stream is from the transalkylation zone of the reactor;

passing an aliquot portion of at least half of the effluent stream as the effluent recycle stream comprising an alkylated aromatic compound to the alkylation zone; and passing the remaining aliquot portion of the effluent stream to be separated to a separation zone, thereby generating an aromatic stream, a product monoalkylated aromatic stream, and a non-product alkylated aromatic stream.

17. The process of claim 16 wherein the alkylation reactor comprises a plurality of alkylation reactors in series, and the recycle stream is divided among the alkylation reactors.

18. The process of claim 16 wherein at least 90% of the effluent stream is passed as a recycle stream.

19. The process of claim 16 wherein the number of olefinic injection ports is between 2 and 6.

* * * * *